United States Patent [19]

Rajagopalan et al.

[11] Patent Number: 5,371,184
[45] Date of Patent: Dec. 6, 1994

US005371184A

[54] RADIOLABELLED PEPTIDE COMPOUNDS

[75] Inventors: Raghavan Rajagopalan, Maryland Heights; Leon R. Lyle, Webster Groves; Thomas J. Dunn, Cedar Hill, all of Mo.

[73] Assignee: Mallinckrodt Medical, Inc., St. Louis, Mo.

[21] Appl. No.: 831,780

[22] Filed: Feb. 5, 1992

[51] Int. Cl.$^5$ ............... C07K 7/10; A61K 43/00; A61K 49/02
[52] U.S. Cl. ............... 530/324; 530/326; 930/22; 930/24; 930/250; 534/10; 534/14
[58] Field of Search ........... 424/1.1, 1.45, 1.69; 530/324, 326, 300; 930/22, 24, 160

[56] References Cited

U.S. PATENT DOCUMENTS

| | | | |
|---|---|---|---|
| 4,746,505 | 5/1988 | Jones et al. | 424/1.1 |
| 4,837,003 | 6/1989 | Nicolotti | 424/1.1 |
| 4,965,392 | 10/1990 | Fritzberg et al. | 424/1.1 X |
| 5,037,630 | 8/1991 | Fritzberg et al. | 424/1.1 |
| 5,080,883 | 1/1992 | Lyle et al. | 424/1.1 |
| 5,175,257 | 12/1992 | Kasina et al. | 424/1.1 X |
| 5,187,264 | 2/1993 | Verbruggen | 424/1.1 |

FOREIGN PATENT DOCUMENTS

| | | |
|---|---|---|
| 0333356 | 9/1989 | European Pat. Off. . |
| 0421366 | 4/1991 | European Pat. Off. . |
| 2225579 | 6/1990 | United Kingdom . |
| WO91/01144 | 2/1991 | WIPO ............ A61K 43/00 |
| 9205154 | 4/1992 | WIPO . |

OTHER PUBLICATIONS

Bryson et al., *Inorg. Chem.* 1990, vol 29, "Protecting Groups in the Preparation of Thiolate Complexes of Techetium", pp. 2948-2951.

Misra et al., *Tetrahedron Letters*, vol. 30, No. 15 (1989) "Synthesis of a Novel Diamino dithiol Ligand . . . ".

*Primary Examiner*—Robert L. Stoll
*Assistant Examiner*—John M. Covert
*Attorney, Agent, or Firm*—Rita D. Vacca

[57] ABSTRACT

A diagnostic composition suitable for administration to a warm-blooded animal comprising hirudin or a molecule capable of interacting with the hirudin receptor labeled with a radionuclide by means of a chelate ligand capable of administration to an animal to produce reliable visual imaging of thrombus.

8 Claims, No Drawings

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Hirudin
        ( B ) STRAIN: Human ( x i ) SEQUENCE DESCRIPTION: SEQ ID NO:1:

```
Ile Thr Tyr Thr Asp Cys Thr Glu Ser Gly Gln Asn Leu Cys Leu Cys
 1               5                  10                  15
Glu Gly Ser Asn Val Cys Gly Lys Gly Asn Lys Cys Ile Leu Gly Ser
                20                  25                  30
Asn Gly Lys Gly Asn Gln Cys Val Thr Gly Gly Gly Thr Pro Lys Pro
                35                  40                  45
Glu Ser His Asn Asn Gly Asp Phe Glu Glu Ile Pro Glu Glu Tyr Leu
            50                  55                  60
Gln
65
```

( 2 ) INFORMATION FOR SEQ ID NO: 2:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein -continued (iii) HYPOTHETICAL: NO (vi) ORIGINAL SOURCE:
  (A) ORGANISM: Hirudin
  (B) STRAIN: Human (xi) SEQUENCE DESCRIPTION: SEQ ID NO: 2:

Phe Pro Arg Pro Gly Gly Gly Gly Asn Gly Asp Phe Glu Glu Ile Pro
1               5                   10                  15

Glu Glu Tyr Leu
            20

(2) INFORMATION FOR SEQ ID NO: 3:

(i) SEQUENCE CHARACTERISTICS:
    (A) LENGTH: 23 amino acids
    (B) TYPE: amino acid
    (D) TOPOLOGY: linear (ii) MOLECULE TYPE: protein (iii) HYPOTHETICAL: NO (vi) ORIGINAL SOURCE:
    (A) ORGANISM: Hirudin
    (B) STRAIN: Human (xi) SEQUENCE DESCRIPTION: SEQ ID NO: 3:

Phe Pro Arg Pro Gly Gly Gly Gly Asn Gly Asp Phe Glu Glu Ile Pro
1               5                   10                  15

Glu Glu Tyr Leu Gly Gly Lys
            20

(2) INFORMATION FOR SEQ ID NO: 4:

(i) SEQUENCE CHARACTERISTICS:
    (A) LENGTH: 23 amino acids
    (B) TYPE: amino acid
    (D) TOPOLOGY: linear (ii) MOLECULE TYPE: protein (iii) HYPOTHETICAL: NO (vi) ORIGINAL SOURCE:
    (A) ORGANISM: Hirudin
    (B) STRAIN: Human (xi) SEQUENCE DESCRIPTION: SEQ ID NO: 4:

Phe Pro Arg Pro Gly Gly Gly Gly Asn Gly Asp Phe Glu Glu Ile Pro
1               5                   10                  15

Glu Glu Tyr Leu Gly Gly Cys
            20

RADIOLABELLED PEPTIDE COMPOUNDS

FIELD OF THE INVENTION

This invention relates generally to novel compounds for use in diagnostic tissue imaging and more particularly, to site specific radiolabelled peptides, to methods of preparing such site specific radiolabelled peptides, and to pharmaceutical compositions comprising these site specific radiolabelled peptides for diagnostic imaging.

BACKGROUND OF THE INVENTION

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which, upon introduction to a biological subject, become localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent designed to target the specific organ or tissue site, various auxiliary agents which affix the radionuclide to the carrier, water or other delivery vehicles suitable for injection into, or aspiration by, the patient, such as physiological buffers, salts, and the like. The carrier agent attaches or complexes the radionuclide to the peptide carrier agent, which results in localizing the radionuclide being deposited in the location where the carrier agent concentrates in the biological subject.

Technetium-99m($^{99m}$Tc) is a radionuclide which is widely known for its uses in tissue imaging agents. Due to its safety and ideal imaging properties, this radionuclide is conveniently available commercially in the oxidized pertechnetate form ($^{99m}$TcO$_4$⁻) hereinafter "pertechnetate-Tc99m". However, pertechnetate will not complex with the most commonly used biological carriers for radionuclide tissue imaging. Thus, technetium-labelled imaging agents are generally prepared by admixing a pertechnetate-Tc99m isotonic saline solution, a technetium reductant (reducing agent) such as stannous chloride or sodium dithionite, and a chelate conjugated to the desired peptide carrier agent for targeting the organ of interest. Alternatively, an intermediate transfer liquid-technetium 99m complex may be prepared prior to addition to the chelate-biological molecule to maintain the oxidation state within a desired level. Examples of such include 99m Tc-tartrate or 99m Tc-gluconate.

Another problem is that technetium-containing scintigraphic imaging agents are known to be unstable in the presence of oxygen, primarily since oxidation of the reductant and/or the technetium-99m destroys the reduced technetium-99m/targeting carrier complex. Accordingly, such imaging agents are generally made oxygen-free by saturating the compositions with oxygen-free nitrogen gas or by preparing the agents in an oxygen-free atmosphere. Stabilization of imaging agents can also be achieved through chemical means. U.S. Pat. No. 4,232,000, Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980 discloses the use of gentisic acid as a stabilizer.

SUMMARY OF THE INVENTION

The present invention discloses novel radiolabelled peptide compounds, methods of preparing these compounds, pharmaceutical compositions comprising these compounds and the use of these compounds in kits for the diagnostic imaging of thrombotic diseases. Thrombus hirudin contain large numbers of receptors having a high affinity for hirudin and derivatives thereof.

In diagnostic thrombus imaging, a radiolabelled compound must be easily detectable and highly selective and have low blood binding. High selectivity, which is essential in these compounds means that the diagnostic compound, after having been introduced into the body, accumulates to a greater degree in the target tissue or tissues, i.e. a thrombi, than in surrounding tissues. In using hirudin or derivatives thereof as carrier agents in radiolabelled compounds, the specific high selectivity of the particular peptide used provides for the strong accumulation of the diagnostic compound in the target tissue or tissues, such as in thrombus in the case of hirudin, compared with the concentration thereof in non-target tissues.

The radiolabelled peptide compounds of the present invention employ the hirudin peptide having sequence identification number 1 NH$_2$-Ile-Thr-Thr-Thr-Asp-Cys-Thr-Glu-Ser-Gly-Gln-Asn-Leu-Cys-Leu-Cys-Glu-Gly-Ser-Asn-Val-Cys-Gly-Lys-Gly-Asn-Lys-Cys-Ile-Leu-Gly-Ser-Asn-Gly-Lys-Gly-Asn-Gln-Cys-Val-Thr-Gly-Gly-Gly-Thr-Pro-Lys-Pro-Glu-Ser-His-Asn-Asn-Gly-Asp-Phe-Glu-Glu-Ile-Pro-Glu-Glu-Tyr-Leu-Gln-COOH;

hirulog-1 peptide having sequence identification number 2 NH$_2$-D-Phe-Pro-Arg-Pro-(Gly)$_4$-Asn-Gly-Asp-Phe-Glu-Glu-Ile-Pro-Glu-Glu-Tyr-Leu-COOH;

hirulog-64 peptide having sequence identification number 3 NH$_2$-D-Phe-Pro-Arg-Pro-(Gly)$_4$-Asn-Gly-Asp-Phe-Glu-Glu-Ile-Pro-Glu-Glu-Tyr-Leu-Gly-Gly-Lys-COOH;

hirulog-133 peptide having sequence identification number 4 NH$_2$-D-Phe-Pro-Arg-Pro-(Gly)$_4$-Asn-Gly-Asp-Phe-Glu-Glu-Ile-Pro-Glu-Glu-Tyr-Leu-Gly-Gly-Cys-COOH; and like derivatives.

In targeting particular receptors with radiolabelled hirudin or its derivatives, it is not necessary that the complete sixty-five (65) residue sequence of hirudin (Seq. I.D. No. 1) be present. Binding is thought to reside primarily in the anion binding exosite. Through substitution in the hirudin sequence, including some limited substitutions in the anion binding exosite and perhaps incorporating D-amino acid enantiomorphs, additional useful peptides are developed without affecting the binding specificity and affinity desired. Likewise peptidomimetic molecules may be prepared to duplicate this specific binding function.

In the present invention, the hirudin peptide itself, or a molecule having hirudin receptor specificity, such as hirulog-1 (Seq. I.D. No. 2), hirulog-64 (Seq. I.D. No. 3)

and hirulog-133 (Seq. I.D. No. 4) may be radiolabelled using more than one method. The reaction generally takes place between the amino groups in the peptide and the carbonyl group in the active ester to form an amide bond. In particular, the peptides can be radiolabelled using either a conventional method referred to as "post-formed chelate approach" or by a recent method referred to as "pre-formed chelate approach" developed by Fritzberg et al., U.S. Pat. Nos. 4,965,392 and 5,037,630 incorporated herein by reference. In the "pre-formed approach," the desired ligand is complexed with the radionuclide and then conjugated to hirudin or a molecule having hirudin receptor specificity. In the "post-formed approach," the desired ligand is first conjugated to the peptide and the resulting conjugate is incubated with 99mTc sodium pertechnetate solution obtained from $^{99}$Mo/$^{99m}$Tc generator along with a reducing agent. In the present invention, the latter approach has the additional advantage of allowing preparation of the complex in kit form. Users merely add Na$^{99m}$TcO$_4$ to the ligand-hirudin conjugate or a derivative thereof for labelling to occur.

It is important to note the unique mechanism of the present invention whereby the conjugation reaction will be successful only when the alpha-amino group is not affected. If the alpha-amino group is affected, the specificity and affinity of the peptide is altered. Therefore, in the molecules of the present invention it is important to perform the conjugation while protecting the alpha-amino group possibly by using blocking agents. For example, in the conjugation of hirulog-133, D-phenylalanine must be protected to ensure specificity. Therefore, in the case of labelling hirulog-1, hirulog-64 or hirulog-133 the epsilon-amino group or the sulfhydryl groups are the groups preferably targeted for labelling. Avoiding the deprotonation of the alpha-amino group involved in binding with the receptor prevents the formation of a chelate complex which interferes with the binding site of the peptide and thus protects the peptide's ability to bind to the receptor. In short, in the present invention, binding preferably occurs on the epsilon-amino group in order to avoid interference with the binding specificity of the hirudin peptide or derivatives thereof.

Using either method of labelling the hirudin peptide or its derivatives, any suitable ligand can be used to incorporate the preferred radionuclide metal ion such as technetium, iodine, rhenium, indium, gallium, samarium, holmium, yttrium, copper, or cobalt. The choice of the ligand entirely depends on the type of metal ion desired for diagnostic purposes. For example, if the radionuclide is a transition element such as technetium or rhenium, then ligands containing amine, amide, and thiols are preferred to form a stable complex whereas if the radionuclide is a lanthanide element, then polyaminocarboxyates or phenolate type ligands are preferable.

The above-described unique characteristics of the present invention make radiolabelled hirudin and its derivatives very attractive for diagnostic purposes. The compounds of the present invention may be labelled with any radionuclide favorable for these purposes. For diagnostic purposes the most suitable radionuclides include but are not limited to the transition metals as exemplified by technetium-99m, and copper-62 and.

Due to the unique mechanism employed in the present invention to label by means of a chelate ligand the epsilon amino group of hirudin and avoid the alpha amino group(s) (which would inhibit the ability of hirudin or derivative peptides to bind to its receptor) a significantly advantageous radiolabelled peptide compound for diagnostic imaging of thrombus and thrombotic diseases is achieved.

It is therefore an object of the present invention to provide a selective agent, both for the diagnostic imaging and for the therapeutic treatment of thrombotic diseases containing high-affinity hirudin receptors having a significantly high target to background ratio.

DETAILED DESCRIPTION OF THE INVENTION

The preferred peptide employed in the present invention is a hirudin peptide as described in German Pat. Nos. 136,103 (1902) and 150,805 (1903) incorporated herein by reference or derivatives thereof. The hirudin peptide is radiolabelled using a pre-formed or post-formed methodology. In a preferred embodiment according to the present invention, the hirudin or a molecule having hirudin receptor specificity is first bonded to the N$_3$S aminothiol ligand which is illustrated in FIG. 1

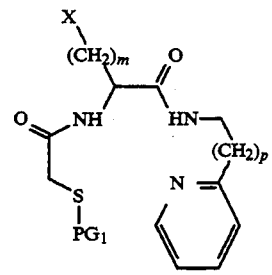

FIG. 1 wherein m is a whole number less than eleven and preferably 3; p is either 0 or 1; PG$_1$ is a suitable sulfur protecting group selected from the group consisting of C$_{1-20}$ S-acyl such as alkanoyl, benzoyl and substituted benzoyl—whereby alkanoyl is preferable, C$_{1-20}$ S-acyl groups such as benzyl, t-butyl, trityl, 4-methoxybenzyl and 2,4-dimethoxybenzyl—whereby 2,4-dimethoxybenzyl is preferable, C$_{1-10}$ alkoxyalkyl such as methoxymethyl, ethoxyethyl and tetrahydropyranyl —whereby tetrahydropyranyl is preferable, carbamoyl, and C$_{1-10}$ alkoxy carbonyl such as t-butoxycarbonyl and methoxycarbonyl—whereby t-butoxycarbonyl is preferable; and X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and C$_{1-10}$ N-alkoxycarbamoyl—whereby N-methylcarbamoyl is preferable.

In another preferred embodiment according to the present invention, hirudin or a molecule having hirudin receptor specificity is bonded to the N$_2$S$_2$ aminothiol ligand which is illustrated in FIG. 2;

FIG. 2 wherein n is a whole number less than eleven and preferably 3; $PG_2$ and $PG_3$ may be the same or different sulfur protecting groups selected from the group consisting of $C_{1-20}$ S-acyl such as alkanoyl, benzoyl and substituted benzoyl—whereby alkanoyl is preferable, $C_{1-20}$ alkyl groups such as benzyl, t-butyl, 4-methoxybenzyl, trityl and 2,4dimethoxybenzyl—whereby 2,4-dimethoxybenzyl is preferable, $C_{1-10}$ alkoxyalkyl such as for example methoxymethyl, ethoxyethyl, and tetrahydropyranyl—whereby tetrahydropyranyl is preferable, carbamoyl and $C_{1-10}$ alkoxycarbonyl such as methoxycarbonyl, ethoxycarbonyl and t-butoxycarbonyl—whereby t-butoxycarbonyl is preferable; and Y is a coupling moiety selected from the group consisting of carboxyl, amino, isocyanate, isothiocyanate, imidate, maleimide, chlorocarbonyl, chlorosulfonyl, succinimidyloxycarbonyl, haloacetyl, and $C_{1-10}$ N-alkoxycarbamoyl—whereby N-methylcarbamoyl is preferable.

In another preferred embodiment of the present invention, hirudin or a molecule having hirudin receptor specificity is conjugated with the ligand illustrated in FIG. 3,

FIG. 3 wherein n varies from 1 to 10, and Y is a coupling moiety selected from the group consisting of carboxyl, amino, isocyanate, isothiocyanate, imidate, maleimide, chlorocarbonyl, chlorosulfonyl, succinimidyloxycarbonyl, haloacetyl, and $C_{1-10}$ N-alkoxycarbamoyl such as N-methoxycarbamoyl and t-butoxycarbamonyl—whereby t-butoxycarbamonyl is preferable; and R is selected from the group consisting of hydrogen and $C_{1-10}$ alkyl such as methyl and t-butyl—whereby t-butyl is preferable.

In another preferred embodiment, the hirudin or a molecule having hirudin receptor specificity can be conjugated with the metal complex illustrated in FIG. 4

FIG. 4 wherein m is a whole number less than eleven and more preferably 3; p is either 0 or 1; X' is a coupling moiety selected from the group consisting of carboxyl, amino, isocyanate, isothiocyanate, imidate, maleimide, chlorocarbonyl, chlorosulfonyl, succininimidyloxycarbonyl, haloacetyl and $C_{1-10}$ N-alkoxycarbamoyl such as N-methoxycarbamoyl and t-butoxycarbamoyl—whereby t-butoxycarbamoyl is preferable and M is a radionuclide suitable for diagnostic imaging or therapeutic use such as technetium, rhenium, copper, cobalt, indium, gallium, samarium, yttrium and holmium.

In another preferred embodiment, the hirudin or a molecule having hirudin receptor specificity can be conjugated with a metal complex as illustrated in FIG. 5 wherein Y' and n are defined the same respectively as Y and n in FIG. 3 and M is defined the same as M in FIG. 4.

FIG. 5

In another preferred embodiment, the hirudin or a molecule having hirudin receptor specificity can be conjugated with a metal complex as shown in FIG. 6.

FIG. 6 wherein Z', q and R are defined the same respectively as Y, n and R of FIG. 3 and M is defined the same as M in FIG. 4.

In another preferred embodiment, the hirudin or a molecule having hirudin receptor specificity can be conjugated with a metal complex as shown in FIG. 7.

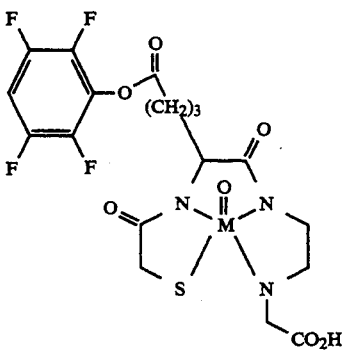

FIG. 7 wherein M is defined the same as M in FIG. 4.

Common esters which have been found useful in this labelling technique are o- and p- nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, thiophenyl, tetrafluorothiophenyl, o-nitro-p-sulfophenyl, N-hydroxyphthalimide and the like. For the most part, the esters will be formed from the reaction of the carboxylate with an activated phenol, particularly, nitro-activated phenols, or a cyclic compound based on hydroxylamine.

The advantages of using sulfur protecting or blocking groups include the fact that a separate step for removal of the sulfur-protective group is not necessary. The protecting groups are displaced from the compound during the labelling in what is believed to be a metal-assisted acid cleavage: i.e., the protective groups are displaced in the presence of a radionuclide at an acid pH and the radionuclide is bound by the chelating compound. The radiolabeling procedure thus is simplified, which is a significant advantage when the chelating compounds are to be radiolabelled in a hospital laboratory shortly before use. Additionally, another advantage of the present invention is that the basic pH conditions and harsh conditions associated with certain known radiolabeling procedures or procedures for removal of other sulfur protected groups are avoided. Thus, base-sensitive groups on the chelating compounds survive the radio-labelling step intact. Suitable sulfur-protecting groups, when taken together with the sulfur atom to be protected, include hemithioacetal groups such as ethoxyethyl, tetrahydrofuranyl, methoxymethyl, and tetrahydropyranyl. Other suitable sulfur protecting groups are $C_{1-20}$ acyl groups, preferably alkanoyl or benzoyl. Other possible formulas for the chelating compounds are described in the European Patent Application assigned publication number 0 284 071 incorporated herein by reference.

Synthesis of the Tc-99m bifunctional chelate and subsequent conjugation to a hirudin peptide, or a derivative thereof, can be performed as described in the European Patent Application assigned publication number 0 284 071 and U.S. Pat. No. 4,965,392 incorporated herein by reference and related technologies as covered by U.S. Pat. Nos. 4,837,003, 4,732,974 and 4,659,839, each incorporated herein by reference.

After purification, technetium-99m labelled hirudin peptide, or derivatives thereof, may be injected into a patient for diagnostic imaging. The technetium-99m hirudin compound is capable of reliably visualizing thrombus within minutes of post-injection. The hirudin peptide when radiolabelled with the technetium-99m triamide thiolate bifunctional chelate is efficacious as an in vivo diagnostic agent for the imaging of thrombus of the type described above. The radiolabelled hirudin compound of the present invention are described in still greater detail in the illustrative examples which follow.

EXAMPLE 1

A solution of hirudin, or derivatives thereof, (0.01 mmol) in 2 mL of carbonate/bicarbonate buffer at pH 8.5 ±0.5 is treated with a solution of 0.1 mmol of the ligand in FIG. 1 (wherein m=2, p=1, $PG_1$ is benzoyl, and X is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired hirudin conjugate.

EXAMPLE 2

A solution of hirudin, or derivatives thereof, (0.01 mmol) in 2 mL of carbonate/bicarbonate buffer at pH 8.5±0.5 is treated with a solution of 0.1 mmol of the ligand in FIG. 2 (wherein n=2, $PG_2$ and $PG_3$ are benzoyl, and Y is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired hirudin conjugate.

EXAMPLE 3

A solution of hirudin, or derivatives thereof, (0.01 mmol) in 2 mL of carbonate/bicarbonate buffer at pH 8.5 ±0.5 is treated with a solution of 0.1 mmol of the ligand in FIG. 3 (wherein q=4, and Z is succinimidyloxycarbonyl) in dimethylformamide (0.5 mL) and the entire mixture is kept at room temperature for 2 hours. The mixture is then diluted with water (2.5 mL) and dialyzed extensively against water. After dialysis, the solution is lyophilized to give the desired hirudin conjugate.

EXAMPLE 4

To 100 uL of a solution containing 5 mg of sodium gluconate and 0.1 mg of stannous chloride in water, 500 ul of 99m-TcO4 (pertechnetate) is added. After incubation at room temperature for about 10 minutes at room temperature, a solution of 500 uL of the hirudin, or derivatives thereof, conjugates (1 mg/mL in 0.1M carbonate/bicarbonate buffer, pH 9.5) in Examples 1 or 2 is then added and the entire mixture is incubated at 37° C. for about 1 hour. The desired labelled peptide is separated from unreacted 99mTc-gluconate and other small molecular weight impurities by gel filtration chromatography (Sephadex G-50) using phosphine buffered physiological saline, (hereinafter PBS), 0.15M NaCl, pH 7.4 as eluent.

EXAMPLE 5

A mixture of gentisic acid (25 mg), inositol (10 mg), and the hirudin, or derivatives thereof, conjugate (500 uL, 1 mg/mL in water) was treated with In-111 indium chloride in 0.05M HCl. The solution was allowed to incubate at room temperature for about 30 minutes. The desired labelled peptide is separated from unreacted In-111 indium salts and other small molecular weight impurities by gel filtration chromatography (Sephadex G-50) using phosphine buffered physiological saline, (PBS), 0.15M NaCl as eluent.

After the hirudin or a derivative thereof is prepared and labelled according to the procedure described above, the compound is used with a pharmaceutically acceptable carrier in a method of performing a diagnostic imaging procedure using a gamma camera or like device. This procedure involves injecting or administering, for example in the form of an injectable liquid, to a warm-blooded animal an effective amount of the present invention and then exposing the warm-blooded animal to an imaging procedure using a suitable detector, e.g. a gamma camera. Images are obtained by recording emitted radiation of tissue or the pathological process in which the radioactive peptide has been incorporated, which in the present case are thrombus, thereby imaging thrombus in the body of the warm-blooded animal. Pharmaceutically acceptable carriers for diagnostic use include those that are suitable for injection or administration such as aqueous buffer solutions, e.g. tris (hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as $Ca^{2+}$, $Na^+$, $K^+$ and $Mg^{2+}$. Other buffer solutions are described in *Remington's Practice of Pharmacy*, 11th edition, for example on page 170. The carriers may contain a chelating agent, e.g. a small amount of ethylenediaminetetraacidic acid, calcium disodium salt, or other pharmaceutically acceptable chelating agents.

The concentration of labeled peptide and the pharmaceutically acceptable carrier, for example in an aqueous medium, varies with the particular field of use. A sufficient amount is present in the pharmaceutically acceptable carrier in the present invention when satisfactory visualization of the thrombi is achievable.

The composition is administered to the warm-blooded animals so that the composition remains in the living animal for about six to seven hours, although shorter and longer residence periods are normally acceptable.

The radiolabelled hirudin compounds of the present invention or derivatives thereof, prepared as described herein, provide means of in vivo diagnostic imaging of thrombus which provides advantages over prior known procedures for diagnosis of thrombotic disease.

After consideration of the above specification, it will be appreciated that many improvements and modifications in the details may be made without departing from the spirit and scope of the invention. It is to be understood, therefore, that the invention is in no way limited, except as defined by the appended claims.

---

We claim:
1. An agent comprising hirudin or a peptide which retains hirudin receptor specificity conjugated with a $N_3S$ ligand having the general structure wherein m is a whole number less than eleven; p is either 0 or 1 $PG_1$ is a sulfur protecting group selected from the group consisting of $C_{1-20}$ S-acyl, $C_{1-20}$ alkyl, $C_{1-10}$ alkoxyalkyl, carbamoyl and $C_{1-10}$ alkoxycarbonyl and X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and $C_{1-10}$ N-alkoxycarbamoyl.

2. The agent of claim 1 labelled in a $^{99m}$Tc-pertechnetate solution containing a reducing agent, a buffering agent, and a transfer ligand such as sodium gluconate or tartarate.

3. The agent of claim 1 labelled in a 186/188 Re-perrhenate solution containing a reducing agent, a buffering agent, and a transfer ligand such as sodium gluconate or tartarate.

4. An agent comprising hirudin or a hirudin fragment having hirudin receptor specificity conjugated with a metal complex having the general structure

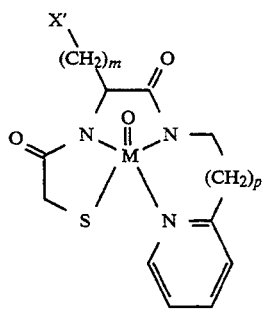

wherein m is a whole number less than eleven; p is either 0 or 1; X is a coupling moiety selected from the group consisting of carboxyl, amino, isocyanate, isothiocyanate, imidate, maleimide, chlorocarbonyl, chlorosulfonyl, succinimidyloxycarbonyl, haloacetyl and $C_{1-10}$ N-alkoxycarbamoyl; and M is technetium, rhenium, gallium, copper or cobalt.

5. The agent of claim 4 labelled in a $^{99m}$Tc-pertechnetate solution containing a reducing agent, a buffering agent, and a transfer ligand such as sodium gluconate or tartarate.

6. The agent of claim 4 labelled in a 186/188 Re-perrhenate solution containing a reducing agent, a buffering agent, and a transfer ligand such as sodium gluconate or tartarate.

7. The agent of claim 4, wherein M is $^{99m}$technetium.

8. The agent of claim 4, wherein M as rhenium-186 or rhenium-188.

* * * * *